(12) United States Patent
Silver et al.

(10) Patent No.: US 7,800,751 B1
(45) Date of Patent: Sep. 21, 2010

(54) DENSE PATTERN MULTIPLE PASS CELLS

(75) Inventors: Joel A. Silver, Santa Fe, NM (US); David S. Bomse, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 878 days.

(21) Appl. No.: 11/678,943

(22) Filed: Feb. 26, 2007

Related U.S. Application Data

(60) Provisional application No. 60/777,366, filed on Feb. 27, 2006.

(51) Int. Cl.
*G01N 1/10* (2006.01)
*G01N 21/00* (2006.01)

(52) U.S. Cl. ........................ 356/246; 356/440
(58) Field of Classification Search ........................ None
See application file for complete search history.

(56) References Cited

U.S. PATENT DOCUMENTS

| | | | |
|---|---|---|---|
| 3,253,226 A | 5/1966 | Herriott et al. | |
| 4,017,185 A | 4/1977 | Chupp | |
| 4,127,329 A | 11/1978 | Chang et al. | |
| 4,676,639 A | 6/1987 | Van Wagenen | |
| 4,783,789 A | 11/1988 | Higgins | |
| 4,934,816 A | 6/1990 | Silver et al. | |
| 5,291,265 A | 3/1994 | Kebabian | |
| 5,550,375 A | 8/1996 | Peters et al. | |
| 5,726,752 A | 3/1998 | Uno et al. | |
| 5,734,165 A | 3/1998 | Unal et al. | |
| 6,087,181 A | 7/2000 | Cong | |
| 6,654,163 B1 | 11/2003 | Du et al. | |
| 6,940,600 B1 | 9/2005 | Smith | |
| 7,012,696 B2 | 3/2006 | Orr et al. | |
| 7,307,716 B2 | 12/2007 | Silver | |
| 7,477,377 B2 * | 1/2009 | Silver | 356/246 |
| 7,616,316 B1 | 11/2009 | Silver et al. | |
| 2002/0185603 A1 | 12/2002 | Daly et al. | |

(Continued)

FOREIGN PATENT DOCUMENTS

DE 29 06 536 9/1980

(Continued)

OTHER PUBLICATIONS

Chernin, S. M. et al., "Optical Multipass Matrix Systems", *Appl. Opt.*, vol. 30, No. 1, Jan. 1991, 51-58.

(Continued)

*Primary Examiner*—Gregory J Toatley, Jr.
*Assistant Examiner*—Amanda H Merlino
(74) *Attorney, Agent, or Firm*—Jeffrey D. Myers; Samantha A. Updegraff; Peacock Myers, P.C.

(57) ABSTRACT

An optical cell and a method of operating an optical cell comprising employing a first mirror comprising a first hole therein at approximately a center of the first mirror and through which laser light enters the cell, employing a second mirror comprising a second hole therein at approximately a center of the second mirror and through which laser light exits the cell, and forming a Lissajous pattern of spots on the mirrors by repeated reflection of laser light entering the cell.

20 Claims, 4 Drawing Sheets

U.S. PATENT DOCUMENTS

2004/0169863 A1    9/2004    Kawate

FOREIGN PATENT DOCUMENTS

DE    102 16 047 A1    10/2003
FR    2 767 195    2/1999

OTHER PUBLICATIONS

Hao, Lu-Yuan et al., "Cylindrical Mirror Multipass Lissajous System for Laser Photoacoustic Spectroscopy" *Rev. Sci. Instrum.*, vol. 73, No. 5 May 2002.

Mittenzwey, K-H et al., "A Portable Absorption-Fluorometer for Detection of Organic Substances in Fluids", *Fresenius J. Anal. Chem.*, vol. 355 1996, 742-744.

Salour, Michael M. et al., "Multipass Optical Cavities for Laser Spectroscopy", *Laser Focus* Oct. 1977, 50-55.

Sigrist, M. W. et al., "Laser Spectroscopic Sensing of Air Pollutants", *Proc. SPIE*, vol. 4063, 2000, 17-25.

Abdullin, R. M., et al., "Use of an Integrating Sphere as a Multipass Optical Cell", *Sov. J. Opt. Technol.*, vol. 55. No. 3, (Mar 1988),139-141.

Altmann, J., et al., "Two-Mirror Multipass Absorption Cell", *Appl. Opt.*, vol. 20, No. 6, (Mar. 15, 1981),995-999.

Herriott, Donald R., et al., "Folded Optical Delay Lines", *Appl. Opt.*, vol. 4, No. 8, (Aug. 1965),883-889.

Herriott, Donald R., et al., "Off-Axis Paths in Spherical Mirror Interferometers", *Appl. Opt.*, vol. 3, No. 4, (Apr. 1964),523-526.

McManus, J. B., et al., "Astigmatic Mirror Multipass Absorption Cells for Long-Path-Length Spectroscopy", *Appl. Opt.*, vol. 34, No. 18, (Jun. 20 1995),3336-3348.

McManus, J. B., et al., "Narrow Optical Interference Fringes for Certain Setup Conditions in Multipass Absorption Cells of the Herriott Type", *Appl. Opt.*, vol. 29, No. 7, (Mar. 1, 1990),898-900.

Silver, Joel A., et al., "Near-infrared diode laser airborne hygrometer", *Rev. Sci. Instrum.*, vol. 65, No. 5,(May 1994), 1691-1694.

Silver, Joel A., "Simple dense-pattern optical multipass cells", *Applied Optics*, vol. 44, No. 31,(Nov. 1, 2005),6545-6556.

Trutna, W. R., et al., "Multiple-Pass Raman Gain Cell", *Applied Optics*, vol. 19, No. 2, (Jan. 15, 1980),301-312.

White, John U., "Long Optical Paths of Large Aperture", *J. Opt. Soc. Am.*, vol. 21, (May 1942),285-288.

Yariv, Amnon, "The Propogation of Rays and Spherical Waves", *Introduction to Optical Electronics*, Holt, Reinhart, and Winston, Inc., New York, Chap. 2, (1971),18-29.

\* cited by examiner

DENSE PATTERN MULTIPLE PASS CELLS

CROSS-REFERENCE TO RELATED APPLICATIONS

This application claims priority to and the benefit of the filing of U.S. Provisional Patent Application Ser. No. 60/777,366, entitled "Improvements to Dense Pattern Multiple Pass Cells", filed on Feb. 27, 2006, and the specification and claims thereof are incorporated herein by reference.

STATEMENT REGARDING FEDERALLY SPONSORED RESEARCH OR DEVELOPMENT

The U.S. government has a paid-up license in this invention and the right in limited circumstances to require the patent owner to license others on reasonable terms as provided for by the terms of Small Business Research (SBIR) Contract No. DE-FG02-03ER83779 awarded by the U.S. Department of Energy.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to creation and use of long folded optical paths in a compact structure for use with lasers in making optical measurements or systems.

2. Description of Related Art

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

Multiple pass optical cells with dense spot patterns are useful for many applications, especially when the cell volume must be minimized relative to the optical path length. Present methods to achieve these dense patterns can use matched pairs of either astigmatic mirrors or cylindrical mirrors. In both cases, the optical beam exiting the cell needs to be separated from the incoming beam, which enters the cell through the center of the front mirror. This separation is difficult due to the small angle between the beams. This invention describes a new, simple approach to collect and measure the output beam intensity using a separate hole in the center of the rear mirror.

Multiple pass optical cells are used to achieve very long optical path lengths in a compact footprint and have been extensively used for absorption spectroscopy (White, J. U., "Long Optical Paths of Large Aperture," *J. Opt. Soc. Am.*, vol. 32, pp 285-288 (May 1942); Altmann, J. R. et al., "Two-mirror multipass absorption cell," *Appl. Opt.*, vol. 20, No. 6, pp 995-999 (15 Mar. 1981)), laser delay lines (Herriott, D. R., et al., "Folded Optical Delay Lines," *Appl. Opt.*, vol. 4, No. 8, pp 883-889 (August 1965)), Raman gain cells (Trutna, W. R., et al., "Multiple-pass Raman gain cell," *Appl. Opt.*, vol. 19, No. 2, pp 301-312 (15 Jan. 1980)), interferometers (Herriott, D. H., et al., "Off-Axis Paths in Spherical Mirror Interferometers," *Appl. Opt.*, vol. 3, No. 4, pp 523-526 (April 1964)) and other resonators (Yariv, A., "The Propagation of Rays and Spherical Waves," from *Introduction to Optical Electronics*, Holt, Reinhart, and Winston, Inc., New York (1971), Chap. 2, pp 18-29).

These cells have taken the form of White cells (White, J. U., "Long Optical Paths of Large Aperture," *J. Opt. Soc. Am.*, vol. 32, pp 285-288 (May 1942)), integrating spheres (Abdullin, R. M. et al., "Use of an integrating sphere as a multiple pass optical cell," *Sov. J. Opt. Technol.*, vol. 55, No. 3, pp 139-141 (March 1988)), and stable resonator cavities (Yariv, A., "The Propagation of Rays and Spherical Waves," from *Introduction to Optical Electronics*, Holt, Reinhart, and Winston, Inc., New York (1971)).

The stable resonator is typified by the design of Herriott (Herriott, D. H., et al., "Off-Axis Paths in Spherical Mirror Interferometers," *Appl. Opt.*, vol. 3, No. 4, pp 523-526 (April 1964)). The simplest such Herriott cell consists of two spherical mirrors of equal focal lengths separated by a distance d less than or equal to four times the focal lengths f of the mirrors. This corresponds to stable resonator conditions. A collimated or focused laser beam is injected through the center of a hole in one of the mirrors, typically at an off-axis location near the mirror edge. The beam is periodically reflected and refocused between these mirrors and then exits through the center of the input hole (defining the re-entrant condition) after a designated number of passes N, in a direction (slope) that is different from the entry slope. As a result, the total optical path traversed in the cell is approximately N×d. The pattern of reflected spots observed on the each mirror in these cells forms an ellipse. Re-entrant conditions for spherical mirror Herriott cells are restricted by certain predetermined ratios of the mirror separation d to the focal length f, and the location and slope of the input beam. For any re-entrant number of passes N, all allowed solutions are characterized by a single integer M. Thorough descriptions for the design, setup and use of these cells are given by Altmann (Altmann, J. R., et al., "Two-mirror multipass absorption cell," *Appl. Opt.*, vol. 20, No. 6, pp 995-999 (15 Mar. 1981)) and McManus (McManus, J. B., et al., "Narrow optical interference fringes for certain setup conditions in multipass absorption cells of the Herriott type," *Appl. Opt.*, vol. 29, No. 7, pp 898-900 (1 Mar. 1990)).

When the cell volume must be minimized relative to the optical path length or where a very long optical path (>50 m) is desired, it is useful to increase the density of passes per unit volume of cell. The conventional spherical mirror Herriott cell is limited by the number of spots one can fit along the path of the ellipse without the spot adjacent to the output hole being clipped by or exiting that hole at a pass number less than N. This approximately restricts the total number of passes to the circumference of the ellipse divided by the hole diameter, which in turn is limited by the laser beam diameter. For a 25-mm radius mirror with a relatively small 3-mm diameter input hole located 20 mm from the center of the mirror, a maximum of about $(\pi \times 2 \times 20)/3 \approx 40$ spots, or 80 passes is possible at best. Generally the hole is made larger to prevent any clipping of the laser input beam that might lead to undesirable interference fringes, and typical spherical Herriott cells employ less than 60 passes.

Herriott (Herriott, D. R. and Schulte, H. J., "Folded Optical Delay Lines," *Appl. Opt.*, vol. 4, No. 8, pp 883-889 (August 1965)) demonstrated that the use of astigmatic mirrors could greatly increase the spot density, and hence optical path length, in the cell. Each mirror has different finite focal lengths ($f_x$ and $f_y$) along orthogonal x and y axes, and the mirrors are aligned with the same focal lengths parallel to one another. The resulting spots of each reflection on the mirrors create precessions of ellipses to form Lissajous patterns. Since these patterns are distributed about the entire face of each mirror, many more spots can be accommodated as compared to a cell with spherical mirrors. McManus (McManus, et al., "Astigmatic mirror multipass absorption cells for long-path-length spectroscopy," Appl. Opt., vol. 34, No. 18, pp 3336-3348 (20 Jun. 1995)) outlines the theory and behavior of this astigmatic Herriott cell and shows that the density of passes can be increased by factors of three or more over spherical mirror cells. For these astigmatic mirror cells, light is injected through a hole in the center of the input mirror. Allowed solutions for re-entrant configurations are characterized by a pair of integer indices $M_x$ and $M_y$, since there are now two focal lengths present along orthogonal axes.

Useful operation, however, is limited by severe design constraints. First of all, both $M_x$ and $M_y$ must simultaneously meet re-entrant conditions. For a desired N and variable distance d, the focal lengths $f_x$ and $f_y$, must be specified to a tolerance of 1 part in $10^4$. Since mirrors can rarely be manufactured to such tolerances, this cell as originally proposed is impractical for routine use. Kebabian (U.S. Pat. No. 5,291,265 (1994)) devised a method to make the astigmatic cell usable. However, his approach still remains difficult to achieve in practice and requires complex calculations and skill to get to the desired pattern. Furthermore, the astigmatic mirrors must still be custom made and cost many thousands of dollars for a single pair.

Recently, Silver (Silver, J. A., "Simple Dense Pattern Optical Multipass Cells," Appl. Opt., vol. 34, No. 31, pp. 6545-6556 (1 Nov. 2005); U.S. patent application Ser. No. 10/896,608) invented a simpler, lower cost and more easily aligned dense pattern multiple pass cell using a pair of cylindrical mirrors. While the exact formulas for describing this cell are different from the astigmatic cell, both are characterized by the total number of passes N before re-entry and by integers $M_x$ and $M_y$ that characterize the number of half-rotations of the spot pattern (in polar co-ordinates) before exiting the cell.

The present invention operates by introducing a separate exit hole in the middle of the rear mirror, whereby the exit beam can be well separated from the entrance beam, and that this exit spot location is invariant to the cell configuration in terms of the designed number of passes or spot pattern. This added versatility permits the use of a wider variety of detectors and requires fewer optical components to collect the output optical beam.

BRIEF SUMMARY OF THE INVENTION

The present invention is of an optical cell and a method of operating an optical cell, comprising: employing a first mirror comprising a first hole therein at approximately a center of the first mirror and through which laser light enters the cell; employing a second mirror comprising a second hole therein at approximately a center of the second mirror and through which laser light exits the cell; and forming a Lissajous pattern of spots on the mirrors by repeated reflection of laser light entering the cell. In the preferred embodiment, the laser light exits the cell after half the number of passes in which the laser light would exit the cell from the first hole if the second hole did not exist. The mirrors are preferably astigmatic or cylindrical mirrors, and if cylindrical most preferably have a non-zero twist angle with respect to one another.

The invention is also of an optical cell and a method of operating an optical cell, comprising: employing a first cylindrical mirror comprising a first hole therein through which laser light enters the cell; employing a second cylindrical mirror comprising a second hole therein through which laser light exits the cell; adjusting the mirrors to have a non-zero twist angle with respect to one another; and forming a Lissajous pattern of spots on the mirrors by repeated reflection of laser light entering the cell. In the preferred embodiment, the first hole is approximately at a center of the first mirror and the second hole is approximately at a center of the second mirror. Most preferably, the laser light exits the cell after half the number of passes in which the laser light would exit the cell from the first hole if the second hole did not exist.

The invention is further of an optical cell and a method of operating an optical cell, comprising: employing a first astigmatic mirror comprising a first hole therein through which laser light enters the cell; employing a second astigmatic mirror comprising a second hole therein through which laser light exits the cell; and forming a Lissajous pattern of spots on the mirrors by repeated reflection of laser light entering the cell. In the preferred embodiment, the first hole is approximately at a center of the first mirror and the second hole is approximately at a center of the second mirror. Most preferably, the laser light exits the cell after half the number of passes in which the laser light would exit the cell from the first hole if the second hole did not exist.

A primary object of the present invention is to generate a long optical path in a compact cell.

Another object of the invention is to keep the cost of this cell low so as to permit widespread commercial availability, feasibility, and usefulness.

Another object of this invention is to make a dense multi-pass cell where one set of mirrors permits a wide range of configurations having many different numbers of allowed passes.

Another object of this invention is to make alignment of the cell for a desired number of optical passes easier, quicker and more reliably accomplished.

Another objective of this invention is to make this dense cell compatible with a wider variety of wavelengths, so that physically large detectors (either by inherent design or because they require large cryogenic cooling components) can be used.

A primary advantage of the present invention is that it can be used in a wide variety of optical applications and can be constructed at significantly lower cost as compared with other dense pattern optical designs.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention is of an improvement to dense multiple pass cells of the Herriott type such that they more easily permit the use of a wider variety of detectors and simplify the optical alignment required for collecting the exiting light. The invention employs a centrally-located exit hole, similar in diameter to the entrance hole, but in the opposed mirror.

For purposes of the specification and claims, a "cylindrical mirror" is one for which one radius of $r_x$ and $r_y$ is substantially infinite, the non-infinite axis being known as the "curved axis" and in this case the curvature along this axis is spherical. This is in contradistinction to a "flat mirror", for which both radii are substantially infinite, and a "spherical mirror" for which both radii are non-infinite and substantially equal. An "astigmatic mirror" is a mirror for which both radii are non-infinite and spherical but not equal, usually deviating only slightly from one another by design.

Figure 1:
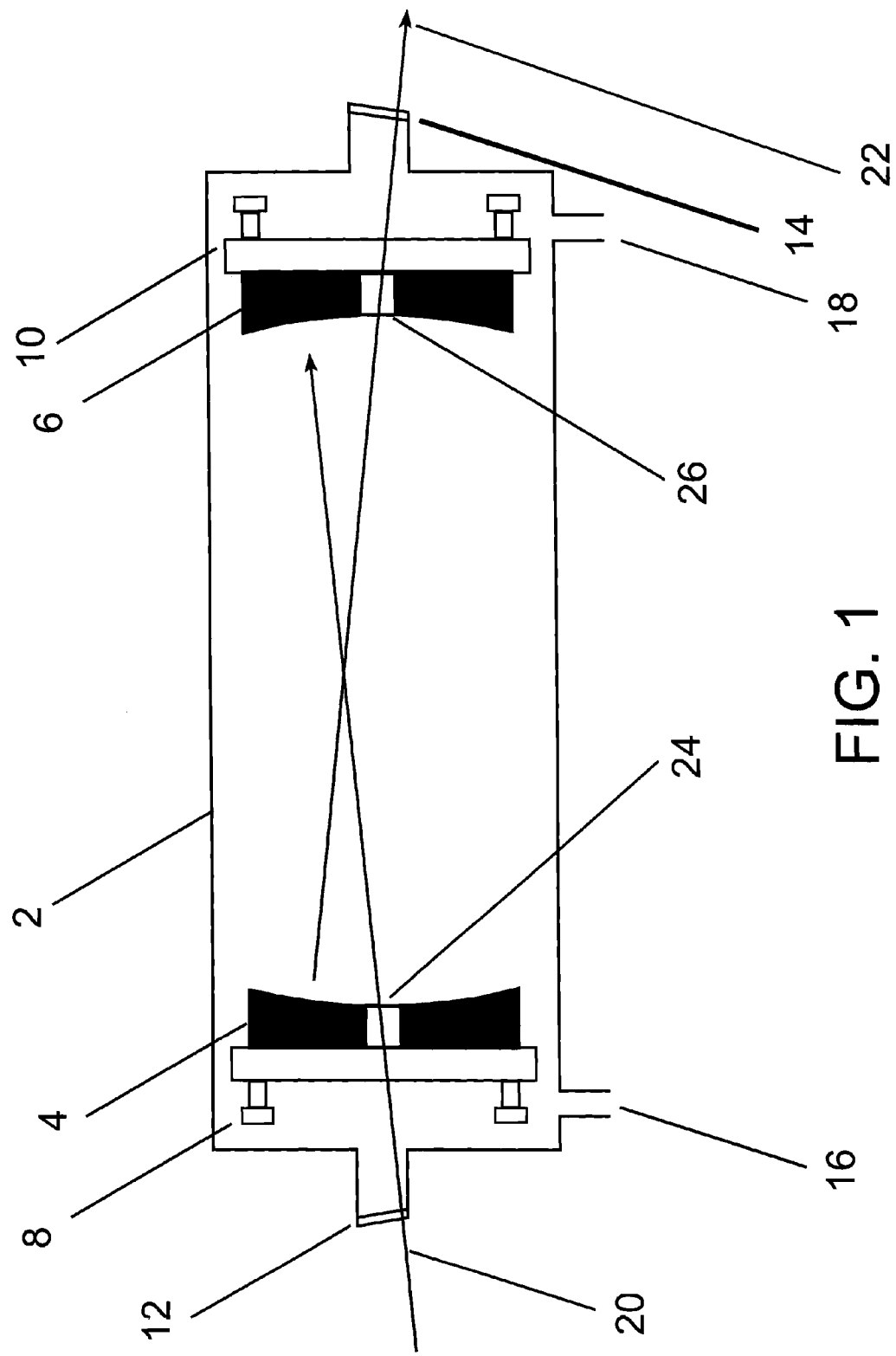
FIG. 1 is a drawing of the preferred embodiment of the present invention.

FIG. 1 is a drawing of the preferred embodiment of the present invention. The entrance mirror 4 and exit mirror 6 comprise the optical cell, separated by distance d. This mirror pair may be either astigmatic or cylindrical, but both mirrors have holes of similar diameter located at their centers. They are attached to adjustable-tilt mirror mounts 8 and 10, respectively, which may be attached to an open frame or located within a closed cell 2. These mounts may also include means for rotating the mirrors about their central axes. These mounts may also have means to adjust the separation distance d. In this example, the cell is sealed, so that flows of sampled gases can be introduced and removed via ports 16 and 18. In a sealed cell the light is transmitted in and out of the cell through windows 12 and 14 suitably transparent to the wavelength of light utilized. The light introduced into the optical cell 20 passes through the hole 24 in mirror 4 and is reflected multiple times by the two mirrors until it exits through hole 26 located in the center of mirror 6.

Figure 2:
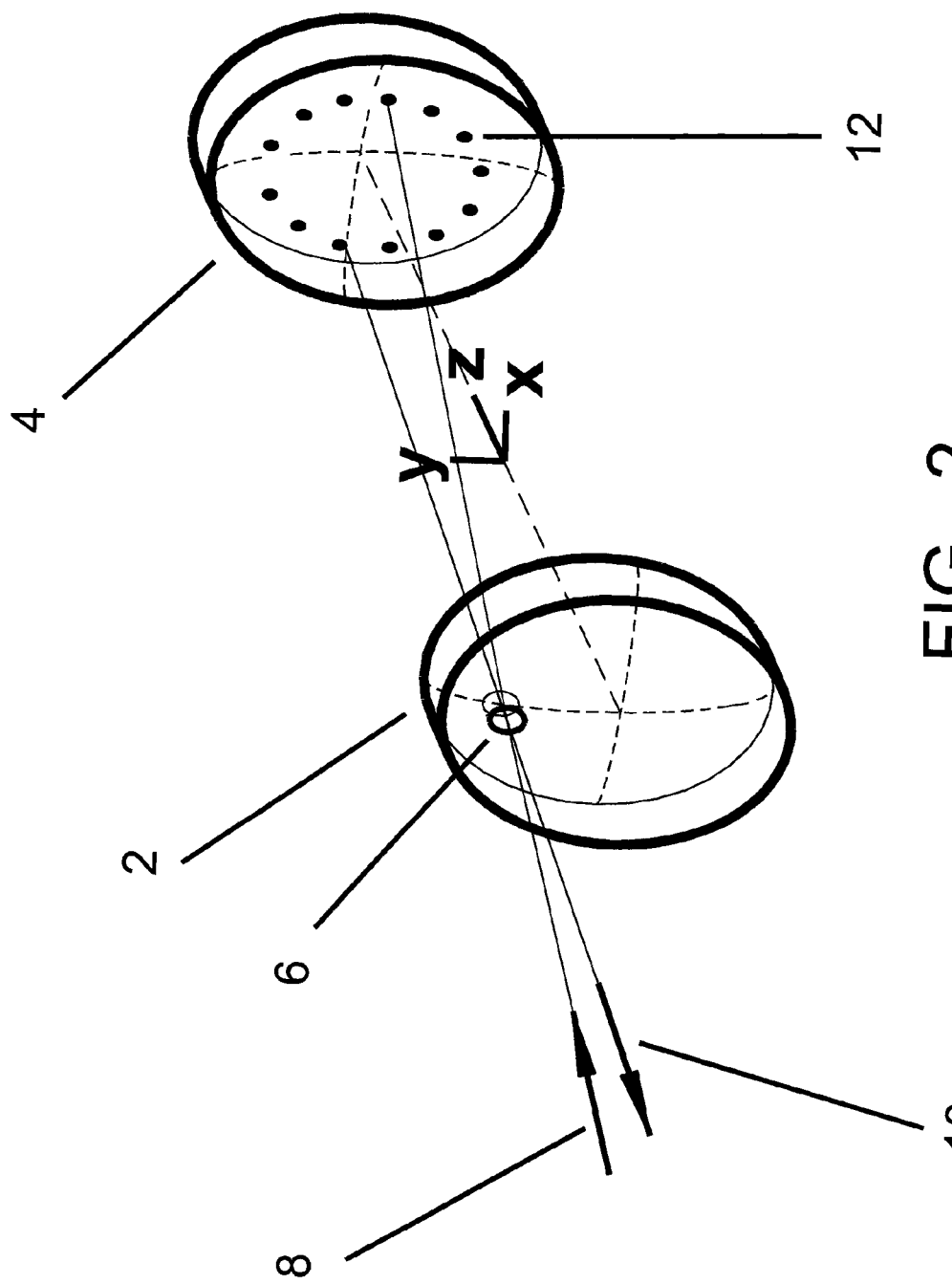
FIG. 2 is a drawing of a conventional Herriott cell with elliptical pattern of spots.

As generally set up (FIG. 2), the conventional Herriott cell comprises two spherical mirrors 2 and 4 of focal length f with an off-axis entrance hole 4 through which the laser beam 8 is injected. For a desired total number of passes N, the focal lengths and mirror separation d are chosen as required (see, e.g., Altmann, J. et al., "Two-mirror multipass absorption cell," *Appl. Opt.* vol. 20, No. 6, pp. 995-999 (15 Mar. 1981)) and the beam is then periodically reflected and refocused such that the beam eventually exits 10 through the input hole 6 (re-entrant condition) but in the opposite direction (slope) of the input beam so as to make possible the placement of a detector or collection optics without obstructing the input beam. In this example there is a pattern 12 of 13 spots on each mirror, for a total of N=26 passes. For a typical cell with 2-inch diameter mirrors and a mirror focal lengths of 20 cm, this pattern corresponds to d=35.2 cm and a total path length of 9.1 m. One can see that the number of passes is limited by the density of spots that can fit on the elliptical pattern that the spots trace out. If either any adjacent spot or if the entering or exiting beams clips the input mirror hole, the scattered light may cause interference fringes (optical etalons), which degrade the detection sensitivity of the measurements (Mc-Manus, J. B. and Kebabian, P. L., "Narrow optical interference fringes for certain setup conditions in multipass absorption cells of the Herriott type," *Appl. Opt.*, vol. 29, No. 7, pp 898-900 (1 Mar. 1990)). Thus the maximum number of passes achievable depends on the beam diameters at the entrance hole and exit, the entrance and exit hole diameters and the density of spots along the ellipse. For this example, an estimation of the maximum N is 62 passes (21 m total path). The separation angle between the input and output beams in this example is 2.8 degrees.

Figure 3:
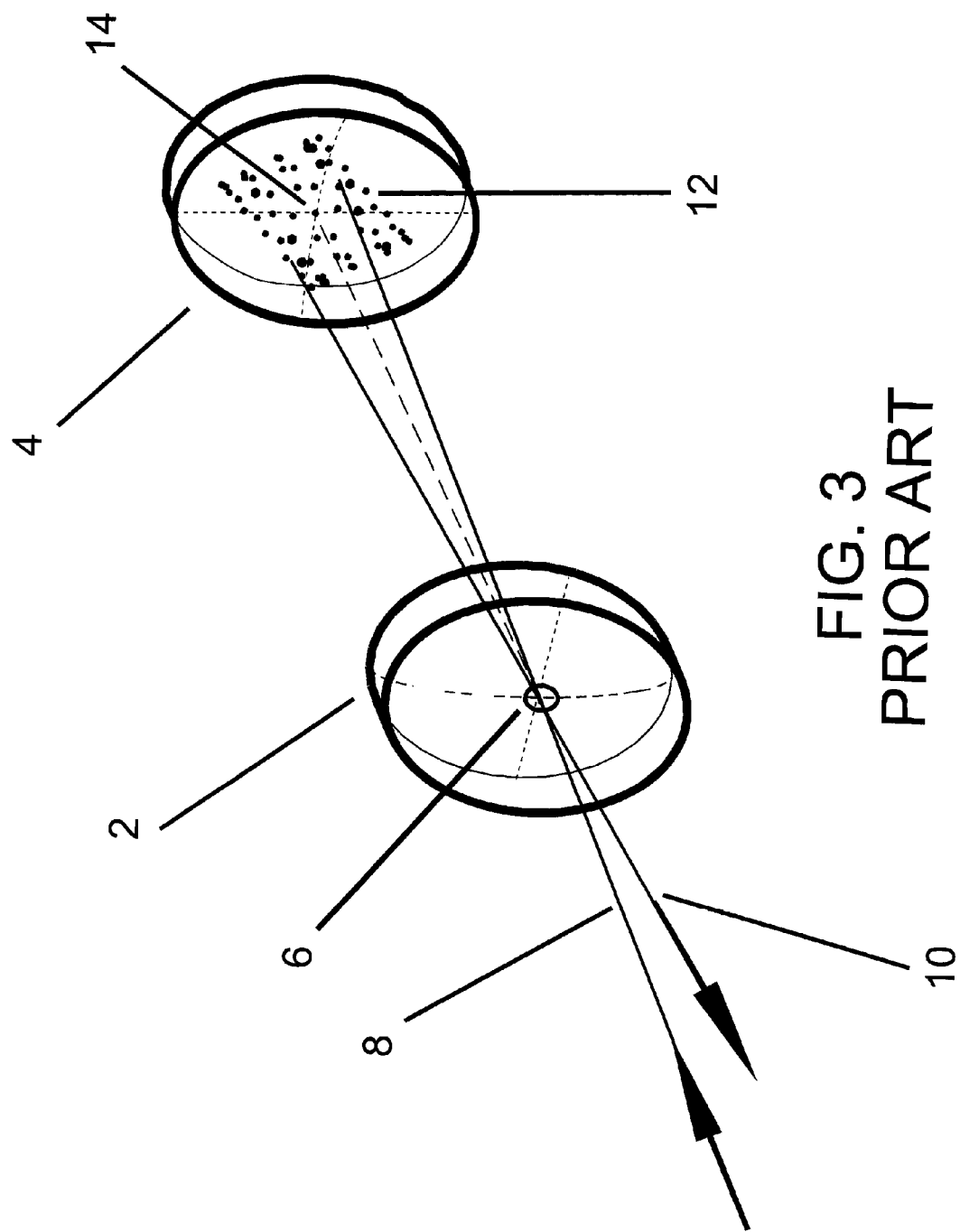
FIG. 3 is a drawing of a cylindrical mirror dense pattern cell with a central hole in the front mirror.

The advantage of using a dense pattern multiple pass cell is seen in FIG. 3, where a Lissajous pattern of spots now efficiently fills the mirror surface. In this case the mirrors 2 and 4 are cylindrical mirrors of 30 cm focal length with their major axes rotated at an angle of 92.3 degrees relative to one another and the mirror separation d=34.0 cm (similar to the example above). The input hole 6 is now located in the center of the front mirror 2. A dense pattern of N=174 passes is shown, generating a much larger total path of 59.1 m. For this re-entrant pattern, $M_x$=44 and $M_y$=50 and from computed positions of the individual spots, the $N/2^{th}$ spot is located centered 14 on the rear mirror, and the input 10 and output beams 12 are separated by an angle of 2.8 degrees. Based on the same criteria as above, spot patterns exceeding 200 passes with total paths exceeding 100 m are possible.

Figure 4:
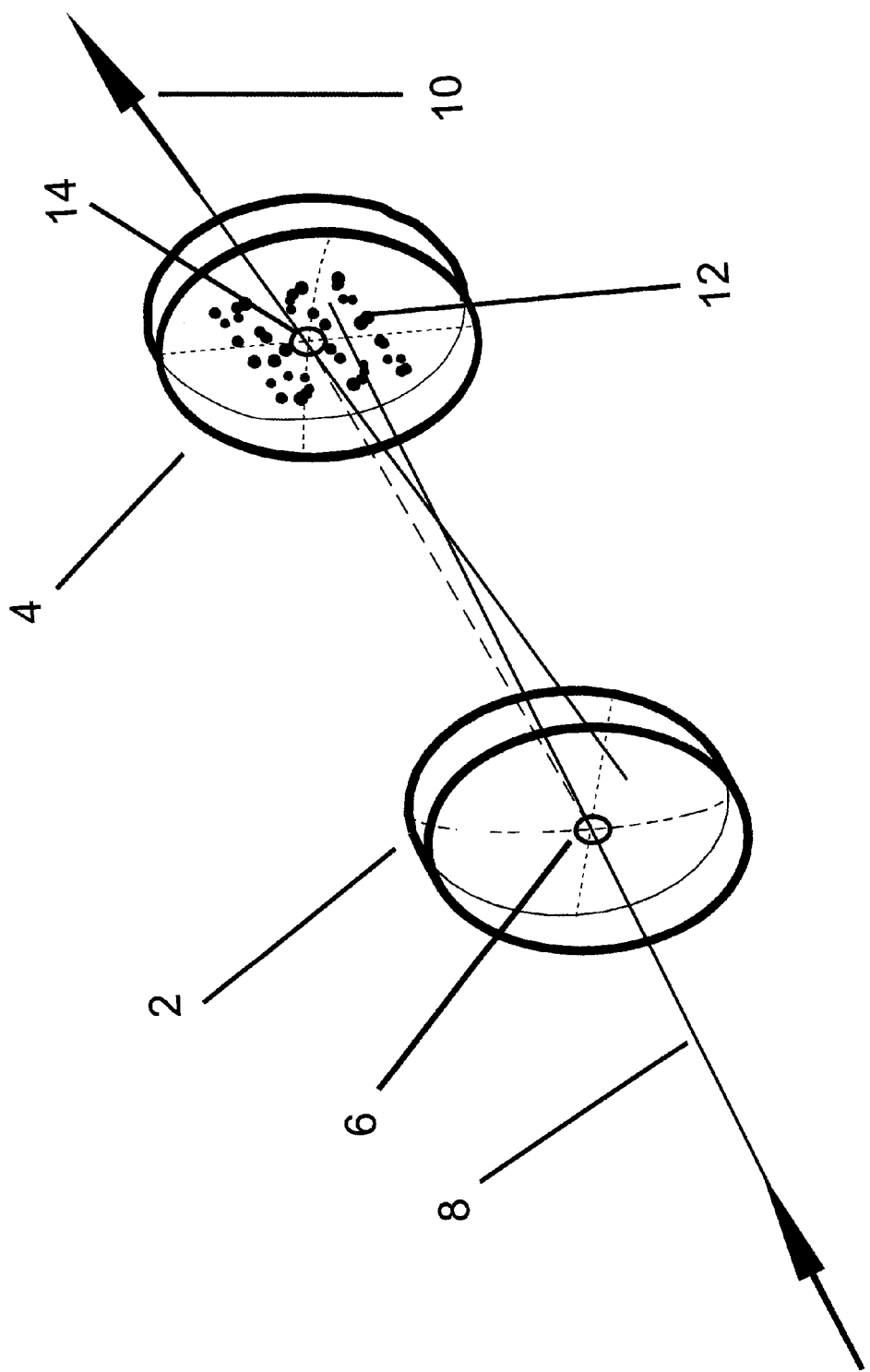
FIG. 4 is a drawing of a cylindrical mirror dense pattern cell with a central hole in both mirrors.

As now shown in FIG. 4, if a second hole 14 is placed in the middle of the rear mirror 4, then the $N/2^{th}$ spot (pass 174/2=87) now exits the optical cell. It imposes no physical constraints concerning placement of detector or collection optics since the input beam and its associated optics are on the other side of the cell. Note that there are now only 43 spots instead of 87 on each mirror. While one experienced in the art would not normally design a cell that uses only half the desired number of passes, in this special case it is exactly what is required to cause the beam to exit at the center of the rear mirror. In order to retrieve the originally desired path length, one needs to now design the cell configuration (focal lengths, mirror separation, rotation of mirrors) for a nominal cell approximately of twice the optical path length desired. In this example, a cell having N=350, $M_x$=92 and $M_y$=100 would give a path of 60.6 m (similar to the configuration above). Denser patterns having design values of N greater than 400 would achieve total paths over 100 m.

For a dense Lissajous pattern that typifies these dense pattern optical cells, one would expect that the spacing between nearest-neighbor spots to be approximately the same. Numerical calculations on a wide variety of dense patterns show that they typically have a narrow distribution of spacings where the variance in the nearest-neighbor spacing distribution typically ranges from 0.4 to 0.6 of the median spacing. This would suggest that the center hole is not, in general, particularly more widely spaced from its closest neighboring spot than any other spot. However, for any desired total number of passes (equivalent to selecting a desired total optical path length), one can numerically determine specific optimal cases where the center to nearest-neighbor distance is close to or exactly the largest separation of any pair of spots. This allows one to configure a rear exiting dense pattern where the potential effect of etalons is minimized. While this selection process works with any dense pattern cell, it is particularly easy to use with the cylindrical mirrors, since they have many more allowed solutions for a desired value of N with any given pair of mirrors.

The significances of using a central-hole rear exiting dense multiple pass configuration include the following:

(1) This approach works for all spot pattern re-entrant conditions where N/2=odd integer, $M_x$=even integer and $M_y$=even integer (Silver, J. A., "Simple Dense Pattern Optical Multipass Cells," *Appl. Opt.*, vol. 34, No. 31, pp. 6545-6556 (1 Nov. 2005)). For a given pair of mirrors, any re-entrant pattern which meets these conditions can use this approach, so that a single set of mirrors can be configured for many different path lengths and total number of passes by simply adjusting the separation and twist angle.

(2) The detector can be placed directly behind the rear mirror and, in some cases, without the need for additional optics. For small photodiodes (UV, visible and near-infrared wavelengths), the detector could even be mounted within the rear mirror output hole. The ability to place the detector very close to the exit results in less beam divergence, lower signal loss and fewer optical components needed to collect the light.

(3) For larger detectors such as photomultiplier tubes or infrared detectors that require cryogenic cooling (and hence have large housings), this approach permits their use closer to the exit with fewer light collection optics. By contrast to the one hole dense pattern systems, where separating the exit beam (which may be diverging) from the input beam only a few degrees apart is difficult to achieve, the two hole method permits much greater compactness of the overall system. For airborne or hand-carried sensors, this factor is significant.

(4) The input slope has no effect on the position of the $N/2^{th}$ spot. Although all of the other spot positions are dependent on the input slope of the beam, this spot is not affected.

(5) While other off-axis exit holes could be used (and in fact have been used for conventional elliptical pattern Herriott cells (Silver and Hovde "Near-Infrared Diode Laser Airborne Hygrometer," Silver, J. A., and Hovde, D. C., *Rev. Sci. Instrum.* Vol. 65, No. 5, pp. 1691-1694 (May 1994), the dense cell is much more sensitive to the position of the Nth spot chosen for exiting. The alignment of dense pattern cells is very complex and intermediate spot positions (i.e., those not the $N^{th}$ or $N/2^{th}$ spot) are unlikely to be accurately predictable so as to pre-drill a hole in the mirror. Also, for dense cells, any of these non-central spots is very likely to be quite close to another spot, raising the issue of interference fringe effects. By contrast, an $N/2^{th}$ spot can be found that is relatively farther spaced from all other spots so as to be less sensitive to this issue and allow a larger hole diameter to minimize beam clipping.

INDUSTRIAL APPLICABILITY

The invention is further illustrated by the following non-limiting example.

Example 1

A pair of commercial 2.54 cm-diameter cylindrical mirrors with f=15 cm (Lambda Research Optics) was assembled on mirror mounts on an optical rail so that the separation could be smoothly varied. The front mirror was mounted on a rotation stage to set the twist angle. For a mirror separation d=13.8 cm and rotation angle of 72.2 degrees, a re-entrant system for N=30 was obtained ($M_x$=8, $M_y$=6). The entrance hole had a diameter of 3.0 mm. The output of a Vertilas 1654 nm vertical cavity diode laser, collimated by a ThorLabs aspheric lens, was pointed into the cell at an angle of 2.1 degrees using two flat turning mirrors. Due to the small footprint of this system, which is designed to make high precision field measurements of fluctuations in ambient methane concentrations, it is quite difficult to collect and measure the re-entrant beam exiting from the cell and image it onto even a small diameter photodiode. By replacing the rear mirror with one that has a 3 mm diameter central hole, we easily recover the output beam (15 passes) by placing the photodiode directly behind the hole in the rear mirror. This configuration has a total path of 2.1 m, sufficient for the very small size of the optical cell. In fact, this system was also reproduced using only 1.25 cm diameter mirrors having 3 mm diameter holes.

Note that the following variations may be employed:

(1) Mirrors of different diameter or focal lengths may be used. As long as a valid re-entrant pattern can be obtained from the mirrors, the central rear mirror hole can be used for output.

(2) The slopes of the entrance beam determine the overall shape and dimension of the spot pattern, but do not affect the number of passes or the location of the N/2th spot, as long as all prior spot positions are still constrained to fall on the reflective surface of the mirror.

(3) Either pairs of astigmatic mirrors or cylindrical mirrors may be used to generate these dense patterns. Both exhibit the property of invariant central N/2 spot position.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An optical cell comprising:
   a first mirror comprising a first hole therein at approximately a center of said first mirror and through which laser light enters the cell; and
   a second mirror comprising a second hole therein at approximately a center of said second mirror and through which laser light exits the cell; and
   wherein said mirrors are configured such that a Lissajous pattern of spots are formed on said mirrors by repeated reflection of laser light entering the cell.

2. The optical cell of claim 1 wherein the laser light exits the cell after half the number of passes in which the laser light would exit the cell from said first hole if said second hole did not exist.

3. The optical cell of claim 1 wherein said mirrors are astigmatic or cylindrical mirrors.

4. The optical cell of claim 3 wherein said mirrors are cylindrical and have a non-zero twist angle with respect to one another.

5. An optical cell comprising:
   a first cylindrical mirror comprising a first hole therein through which laser light enters the cell; and
   a second cylindrical mirror comprising a second hole therein through which laser light exits the cell; and
   wherein said mirrors have a non-zero twist angle with respect to one another and are configured such that a Lissajous pattern of spots are formed on said mirrors by repeated reflection of laser light entering the cell.

6. The optical cell of claim 5 wherein said first hole is approximately at a center of said first mirror and said second hole is approximately at a center of said second mirror.

7. The optical cell of claim 6 wherein the laser light exits the cell after half the number of passes in which the laser light would exit the cell from said first hole if said second hole did not exist.

8. An optical cell comprising:
   a first astigmatic mirror comprising a first hole therein through which laser light enters the cell; and
   a second astigmatic mirror comprising a second hole therein through which laser light exits the cell; and wherein said mirrors are configured such that a Lissajous pattern of spots are formed on said mirrors by repeated reflection of laser light entering the cell.

9. The optical cell of claim 8 wherein said first hole is approximately at a center of said first mirror and said second hole is approximately at a center of said second mirror.

10. The optical cell of claim 9 wherein the laser light exits the cell after half the number of passes in which the laser light would exit the cell from said first hole if said second hole did not exist.

11. A method of operating an optical cell, the method comprising the steps of:
   employing a first mirror comprising a first hole therein at approximately a center of the first mirror and through which laser light enters the cell;
   employing a second mirror comprising a second hole therein at approximately a center of the second mirror and through which laser light exits the cell; and
   forming a Lissajous pattern of spots on the mirrors by repeated reflection of laser light entering the cell.

12. The method of claim 11 wherein the laser light exits the cell after half the number of passes in which the laser light would exit the cell from the first hole if the second hole did not exist.

13. The method of claim 11 wherein the mirrors are astigmatic or cylindrical mirrors.

14. The method of claim 13 wherein the mirrors are cylindrical and have a non-zero twist angle with respect to one another.

15. A method of operating an optical cell, the method comprising the steps of:
   employing a first cylindrical mirror comprising a first hole therein through which laser light enters the cell;
   employing a second cylindrical mirror comprising a second hole therein through which laser light exits the cell;
   adjusting the mirrors to have a non-zero twist angle with respect to one another; and
   forming a Lissajous pattern of spots on the mirrors by repeated reflection of laser light entering the cell.

16. The method of claim 15 wherein the first hole is approximately at a center of the first mirror and the second hole is approximately at a center of the second mirror.

17. The method of claim 16 wherein the laser light exits the cell after half the number of passes in which the laser light would exit the cell from the first hole if the second hole did not exist.

18. A method of operating an optical cell, the method comprising the steps of:
   employing a first astigmatic mirror comprising a first hole therein through which laser light enters the cell;
   employing a second astigmatic mirror comprising a second hole therein through which laser light exits the cell; and
   forming a Lissajous pattern of spots on the mirrors by repeated reflection of laser light entering the cell.

19. The method of claim 18 wherein the first hole is approximately at a center of the first mirror and the second hole is approximately at a center of the second mirror.

20. The method of claim 19 wherein the laser light exits the cell after half the number of passes in which the laser light would exit the cell from the first hole if the second hole did not exist.

* * * * *